US008874201B2

(12) United States Patent
Tokuda et al.

(10) Patent No.: US 8,874,201 B2
(45) Date of Patent: Oct. 28, 2014

(54) INTRACEREBRAL INFORMATION MEASURING DEVICE

(75) Inventors: Takashi Tokuda, Kyoto (JP); Jun Ohta, Souraku-gun (JP)

(73) Assignee: National University Corporation Nara Institute of Science and Technology, Ikoma-shi (JP)

( * ) Notice: Subject to any disclaimer, the term of this patent is extended or adjusted under 35 U.S.C. 154(b) by 676 days.

(21) Appl. No.: 13/121,506

(22) PCT Filed: Sep. 25, 2009

(86) PCT No.: PCT/JP2009/004877
§ 371 (c)(1),
(2), (4) Date: Mar. 29, 2011

(87) PCT Pub. No.: WO2010/038393
PCT Pub. Date: Apr. 8, 2010

(65) Prior Publication Data
US 2011/0178422 A1    Jul. 21, 2011

(30) Foreign Application Priority Data

Sep. 30, 2008  (JP) ................. 2008-251964

(51) Int. Cl.
*A61B 5/0476*  (2006.01)
*A61B 5/0478*  (2006.01)
*A61B 5/00*    (2006.01)
*A61B 5/04*    (2006.01)
*A61B 5/0492*  (2006.01)

(52) U.S. Cl.
CPC ........... *A61B 5/04001* (2013.01); *A61B 5/0478* (2013.01); *A61B 5/0086* (2013.01); *A61B 5/0492* (2013.01)
USPC ....................................... 600/544

(58) Field of Classification Search
None
See application file for complete search history.

(56) References Cited

U.S. PATENT DOCUMENTS

| 2004/0006264 A1 | 1/2004 | Mojarradi et al. |
| 2004/0082875 A1 | 4/2004 | Donoghue et al. |

(Continued)

FOREIGN PATENT DOCUMENTS

| DE | 60 2005 002 498 T2 | 6/2008 |
| EP | 1 614 443 A1 | 1/2006 |

(Continued)

OTHER PUBLICATIONS

"Intracranial Electrode," Unique Medical Co., Ltd., http://www.mmjp.or.jp/unique-medical/newuzncatNo1018b.pdf.

(Continued)

*Primary Examiner* — Charles A Marmor, II
*Assistant Examiner* — Michael J Burrage
(74) *Attorney, Agent, or Firm* — Oliff PLC

(57) ABSTRACT

An intracerebral information measuring device which can be mounted on the head of a subject by simple surgery and which attains measurement of low invasion, high sensitivity, and high resolution is provided. An internally mounted unit is composed of a probe section to be inserted in the brain through a hole having a small diameter bored in the skull of the subject, and a head section integrated with the probe section and to be disposed between the skull and the scalp. The probe section includes an electrode for sensing an action potential. The head section includes a transmitter for wirelessly transmitting signals captured with the electrode to the outside. On the outside of the head, an external measuring unit for receiving the signal transmitted from the head section and reproducing the original signal is provided.

5 Claims, 4 Drawing Sheets

(56) References Cited

U.S. PATENT DOCUMENTS

| | | |
|---|---|---|
| 2005/0015128 A1 | 1/2005 | Rezai et al. |
| 2005/0113744 A1 | 5/2005 | Donoghue et al. |
| 2005/0143790 A1* | 6/2005 | Kipke et al. .................... 607/60 |
| 2005/0203366 A1 | 9/2005 | Donoghue et al. |
| 2006/0009814 A1 | 1/2006 | Schulman |
| 2006/0167530 A1 | 7/2006 | Flaherty et al. |
| 2006/0206172 A1 | 9/2006 | DiMauro et al. |
| 2006/0253166 A1 | 11/2006 | Flaherty et al. |
| 2007/0032738 A1 | 2/2007 | Flaherty et al. |
| 2007/0169333 A1 | 7/2007 | Donoghue et al. |
| 2007/0239235 A1* | 10/2007 | DiMauro et al. ................ 607/88 |

FOREIGN PATENT DOCUMENTS

| | | |
|---|---|---|
| JP | A-2006-230955 | 9/2006 |
| JP | A-2007-289224 | 11/2007 |
| WO | WO 03/061517 A2 | 7/2003 |
| WO | WO 2004/105640 A2 | 12/2004 |
| WO | WO 2005/051167 A1 | 6/2005 |
| WO | WO 2005/092183 A1 | 10/2005 |
| WO | WO 2006/073915 A2 | 7/2006 |

OTHER PUBLICATIONS

International Search Report issued in International Application No. PCT/JP2009/004877 on Dec. 1, 2009 (with translation).

International Preliminary Report on Patentability issued in International Application No. PCT/JP2009/004877 on Mar. 10, 2010. (with translation).

* cited by examiner

SINGLE-CORE PROBE Fig. 3A
SINGLE-CORE SHEATH PROBE Fig. 3B
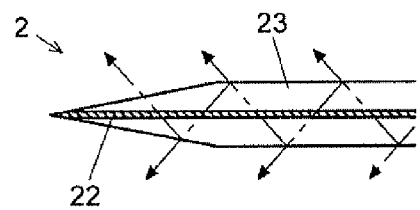
COAXIAL PROBE Fig. 3C
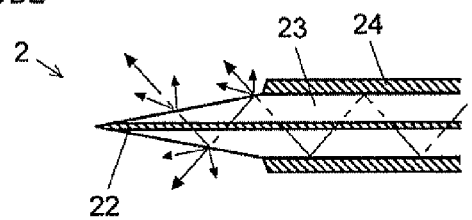
Fig. 4
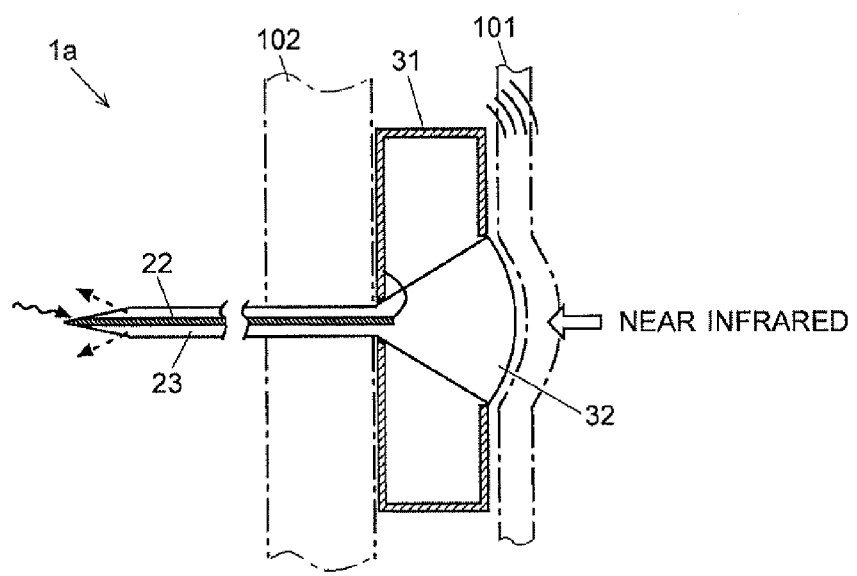

INTRACEREBRAL INFORMATION MEASURING DEVICE

TECHNICAL FIELD

The present invention relates to an intracerebral information measuring device for collecting information relating to the inside of the brain of a subject, such as human beings, experimental animals, domestic animals, pets or other kinds of animals.

BACKGROUND ART

In recent years, the brain science and medial measurement technologies have made remarkable progress. For the purpose of collecting intracerebral information, various kinds of sensing devices and new techniques for imaging cerebral functions have been realized. Intracerebral information measuring devices can be roughly divided into invasive and noninvasive types. Invasive devices require a certain kind of surgery, such as the incision of the scalp or skull of the subject, in order to bring an electrode or similar element in direct contact with the brain. On the other hand, noninvasive devices are designed to indirectly access the brain from outside the subject's head (i.e. through the scalp or skull) to extract certain kinds of intracerebral information.

Many reports have been made on the invasive intracerebral information measuring devices, such as the "Michigan" electrode (developed at the University of Michigan, USA) or the "Utah" electrode (developed at the University of Utah). These electrodes can be used to perform multi-point measurements at the level of cellular size inside the brain. Another example is an intracranial electrode manufactured by a Japanese company, UNIQUE MEDICAL CO., LTD. (Refer to Non-Patent Document 1.) This electrode is officially authorized in Japan as a device for the clinical therapy of epilepsy.

These conventional types of invasive intracerebral information measuring devices are basically designed to be mounted on a brain of the subject after the brain is exposed by incising the skull. Particularly, when the measurement needs to be performed over a wide area of the brain, it is necessary to incise an accordingly large area of the skull. Any surgery including the incision of the skull inherently requires a major operation and hence imposes significant strain on the subject. Furthermore, it is accompanied by high risk of infection or the like.

On the other hand, for the noninvasive measurement of cerebral functions, excellent measurement techniques have been developed, such as the f-MRI (functional magnetic resonance imaging) or optical topography. These techniques have made considerable achievements in the fields of diagnosis and research. For example, the optical topography measurement is capable of measuring the change in a local blood volume in the brain of the subject. Such a technique is useful for the diagnosis of cerebrovascular disease (for example, refer to Patent Document 1). However, due to the restriction that the noninvasive measurement is merely an indirect measurement, it is difficult to improve the resolution, sensitivity or other performances of the measurement. Another problem is that, although the information obtained at a region near the surface of the brain is relatively accurate, it is difficult to obtain information at deeper regions of the brain.

BACKGROUND ART DOCUMENTS

Patent Document

Patent Document 1: JP-A 2007-289224

Non-Patent Document

Non-Patent Document 1: "Intracranial Electrode", website of UNIQUE MEDICAL CO., LTD., [Searched on Sep. 3, 2008]

DISCLOSURE OF THE INVENTION

Problem to be Solved by the Invention

Thus, there is a limit on the noninvasive measurement to achieve high resolution and high sensitivity to meet the diversified and sophisticated needs of recent brain science. Therefore, direct access to the brain is still required. However, it is also important to suppress its invasiveness to the lowest possible degree to facilitate the mounting of the device and reduce the strain on the subject. Furthermore, the device should desirably support both the measurement of a rather limited region and the measurement of a broad area (e.g. the entire brain) since these two types of measurements need to be appropriately performed depending on the use or purpose of the measurement.

Combining an electrical measurement with an optical measurement, such as the optical topography measurement, is useful for the diagnosis of diseases or other purposes since these two types of measurements provide different kinds of information. However, as already stated, it is impossible to obtain information relating to deeper regions of the brain by the conventional optical measurement.

The present invention has been developed in view of the previously described problems. Its main objective is to provide an intracerebral information measuring device which can be mounted on the brain without any major surgery, thereby suppressing the invasiveness as well as lessening the strain on the subject and reducing the risk to the subject, and yet can perform the measurement with high sensitivity and high resolution.

Another objective of the present invention is to provide an intracerebral information measuring device that is applicable to both the local-area measurement and the broad-area measurement, and is also suitable for a long-term measurement.

Still another objective of the present invention is to provide an intracerebral information measuring device capable of concurrently performing both the electrical measurement and the optical measurement on a deeper region of the brain.

Means for Solving the Problems

The present invention aimed at solving the aforementioned objectives is an intracerebral information measuring device for collecting information relating to the inside of the brain of a subject, including:

a) an internally mounted unit including: a probe section being designed to be inserted in the brain or into a sulcus of the brain through a hole bored in the skull of the subject, the probe section having an electrode for capturing at least an electric signal in a surrounding area; and a head section integrated with one end of the probe section, the head section being designed to be held between the skull and the scalp of the subject and having a signal transmitter for wirelessly sending at least an electric signal captured with the electrode to the outside of the scalp; and b) an external measuring unit to be placed outside the scalp of the subject, for receiving the signal sent from the signal transmitter of the head section through the scalp.

The "subject" in the present description includes not only human beings but also experimental animals, domestic animals, pets and other kinds of animals.

In the intracerebral information measuring device according to the present invention, the internally mounted unit may be formed like a thumbtack (or drawing pin). The probe section may be either a rigid part or a flexible part.

To mount the internally mounted unit on the subject, the scalp of the subject is partially incised, and a hole having a diameter slightly greater than that of the probe is bored into the skull. This surgical operation is much easier and needs a shorter period of time than the craniotomy procedure which involves incising the skull. After the hole is bored, the probe section is inserted through that hole to insert the tip of the probe section into the brain or insert it into a sulcus of the brain. The inserting point can be previously chosen by an appropriate method, such as X-ray imaging. The depth of inserting the probe section into the brain can be adjusted by appropriately setting the length of the probe section. For example, it may be stuck into a deep region inside the brain or set at a point near the surface of the brain (e.g. in the cerebral cortex) as needed. In any case, the probe section is pushed into the brain until the head section is stopped by the skull. Subsequently, if necessary, the incised portion of the scalp is sutured to cover the head section.

Thus, only the probe section of the internally mounted unit is located inside the skull of the subject; the head section is also located inside the body but outside the skull of the subject. The external measuring unit is located outside the subject, typically on the surface of the scalp at a position near the head section. When the internally mounted unit is mounted on the subject's head in the previously described manner, the electrode of the probe section captures a faint electric signal generated by the brain in the surrounding area (which is typically brainwaves). The signal transmitter provided in the head section wirelessly sends this signal to the outside. The transmitted signal passes through the scalp, to be received by the external measuring unit outside of the scalp. The external measuring unit reproduces the electric signal generated by the brain.

Particularly, an electric signal generated in a deep region of the brain (e.g. action potential of a nervous tissue) can be detected by adopting a structure in which the electrode is exposed only at the tip of the probe section. Alternatively, a cortical field potential inside the brain can be detected by adopting a structure in which the electrode is exposed over a wide area on the circumferential surface of the probe section.

In one mode of the cerebral information measuring device according to the present invention, the signal transmitter utilizes the radiation from the casing of the head section to transmit signals. In this mode of the device, no electrical circuit for signal transmission is required in the head section. Therefore, the device will be simply structured, inexpensive, and less likely to break down. Even if the internally mounted unit is broken down or damaged, there will be only a minor risk to the subject since no electrical circuit is present inside the subject's body.

In the second mode of the intracerebral information measuring device according to the present invention, the signal transmitter includes a conversion processor for converting the electric signal captured by the electrode into a predetermined form and an antenna for radiating the signal resulting from the conversion.

In the second mode, the head section has a built-in electrical circuit for wirelessly transmitting an electric signal (e.g. brainwaves) obtained with the electrode to the outside. The conversion processor includes a modulator for modulating the signal into a suitable form for the radio transmission through the antenna. In the case where the electric signal obtained with the electrode is transmitted in a digitized form, the head section may further include an analogue-to-digital converter or the like. This configuration is advantageous for performing the measurement at higher levels of sensitivity and resolution since the digitized information is barely influenced by noise or other disturbing factors when transmitted from the internally mounted unit to the external measuring unit. Furthermore, since digitized signals can be transmitted over a long distance, the external measuring unit can be separated from the scalp to some extent. This increases the degree of freedom of the location of the external measuring unit and thereby gives a higher degree of freedom of the subject's motion.

In the case of the second mode, it is necessary to supply an electric power for driving the built-in electrical circuit of the head section. One possibility is to install a battery inside the head section. However, this is disadvantageous for a light-weight design of the head section and a long-term use of the device. In a more preferable configuration, the head section includes a power supplier for generating power by receiving waves radiated from the external measuring unit, and the generated power is used as drive power for the signal transmitter. For such a transfer of power, a technique used in passive IC tags (RFID) is available.

The intracerebral information measuring device according to the present invention may be configured so that both the electric measurement of brainwaves or other signals and an optical measurement corresponding to the optical topography or similar measurement can be performed simultaneously or on a time-share basis. Thus, in a preferable mode of the intracerebral information measuring device according to the present invention, the head section has an optical aperture, and the probe section has a waveguide optically coupled to the optical aperture. Correspondingly, the external measuring unit may preferably include an irradiator for casting near-infrared light for the optical topography measurement through the scalp of the subject onto the head section of the internally mounted unit.

For example, when near-infrared light is generated by the irradiator of the external measuring unit and cast from outside onto the scalp, the light penetrates through the scalp into the optical aperture of the head section located underneath. Then, the light passes through the waveguide into the brain. Thus, an intracerebral region is irradiated with the near-infrared light. In the case of the conventional optical topography measurement, the near-infrared light is cast from outside the subject's head, and only a light reflected by, scattered by or transmitted through a region near the surface of the brain can be obtained. In the present case, the light can be delivered deeper into the brain depending on the inserting depth of the probe section or other conditions.

The waveguide also has the function of receiving the light reflected by, scattered by or transmitted through the brain and guiding the light to the head section. Accordingly, apart from the aforementioned internally mounted unit which is used for delivering light, a second internally mounted unit may be set at a certain distance from the first one so as to make the second unit function as a detector for receiving light through the probe section, for guiding the received light through the waveguide to the head section, and for emitting the light through the optical aperture of the head section to the outside. The emitted light can be received through the scalp by a photo-receiver which is provided, for example, in a second external measuring unit, which measures the intensity of the light.

The head section may include a photoelectric converter for receiving light coming from the probe section through the waveguide and for converting the received light into an electric signal. This electric signal generated by the photoelectric converter can be sent through the signal transmitter consisting of the aforementioned electrical circuit to the external measuring unit. With this configuration, the optical measurement can also be performed with higher sensitivity and resolution.

In the intracerebral information measuring device according to the present invention, the internally mounted unit serves as an electrical and optical access point to deeper regions inside the brain. Accordingly, as described previously, both electrical information and optical information can be extracted from deeper regions inside the brain. Furthermore, the electrode and waveguide can be used in the opposite direction. That is to say, the electrode can be used to give an electrical stimulus to a deep region of the brain; similarly, the waveguide can be used to give an optical stimulus. By combining the electric and optical stimuli, it is possible, for example, to obtain electrical information relating to a change in the brainwaves induced by an optical stimulus, or to obtain optical information relating to a change in the blood flow induced by an electrical stimulus.

Effect of the Invention

With the intracerebral information measuring device according to the present invention, it is possible to obtain various effects as follows:

(1) To mount the internally mounted unit on the subject's head, only a minor surgical operation for creating a small hole in the skull for the insertion of the probe section is required, so that the device can be easily mounted within a short period of time. Furthermore, it considerably reduces the strain on the subject (e.g. a patient or experimental animal) during the mounting process. This allows organic activities of the subject to go smoothly even after the device is mounted, thereby enhancing the stability and correctness of the measurement.

(2) No high-risk factor, such as electrical wiring or circuits, is present inside the brain. Other risky elements are installed outside the skull. Therefore, even if the internally mounted unit is broken down or damaged, the intracerebral tissue will undergo only a minimal adverse effect.

(3) An electrical or optical measurement can be directly performed on an inner region of the brain or on a sulcus of the brain. Particularly, the optical measurement can be performed on a deep region of the brain that has been conventionally difficult to measure. The thereby obtained signals have notable qualities (e.g. high signal-to-noise ratios), which enable the measurement to be performed with high sensitivity and resolution. Therefore, when cerebropathy or encephalopathy of a subject is diagnosed based on the information collected with the intracerebral information measuring device according to the present invention, the diagnosis can be made with higher accuracy and reliability than ever before. It is also possible to find disorders or diseases that have been conventionally difficult to find. Thus, the present invention is useful for the early treatment of cerebral disorders or diseases.

(4) The wireless signal transmission between the internally mounted unit and the external measuring unit gives the subject a high degree of freedom of motion, making it possible to perform a meaningful measurement on a free-moving subject. The internally mounted unit will never be detached and barely damaged due to the motion of the subject, thus allowing a long-term measurement.

BRIEF DESCRIPTION OF THE DRAWINGS

FIGS. 3A-3C are schematic sectional views showing three representative forms of the probe section 2.

FIG. 4 is a schematic sectional view of one form (passive type) of the internally mounted unit using a single-core sheath probe structure.

BEST MODE FOR CARRYING OUT THE INVENTION

Figure 1:
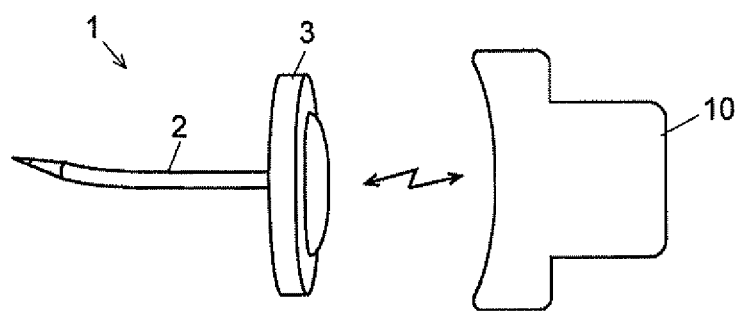
FIG. 1 is an external view showing the basic construction of an intracerebral information measuring device according to one embodiment of the present invention.
Figure 2:
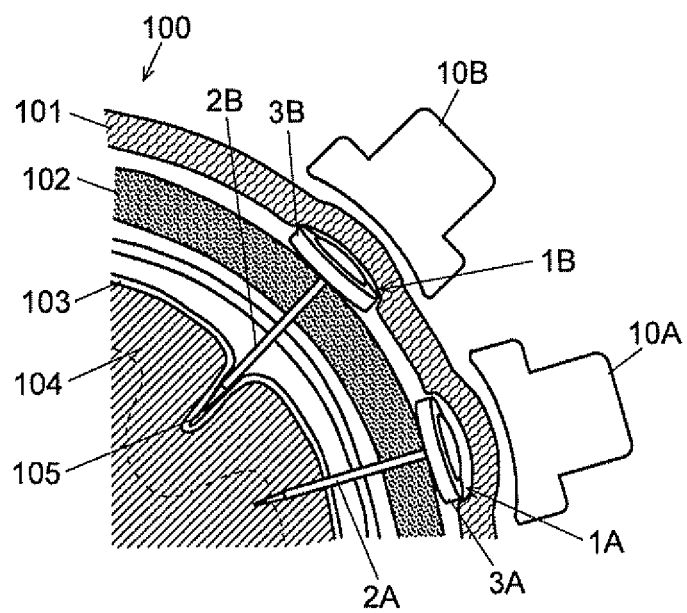
FIG. 2 is a schematic sectional view of a subject's head with the intracerebral information measuring device of the present embodiment mounted thereon.

One embodiment of the intracerebral information measuring device according to the present invention is hereinafter described in detail with reference to the attached drawings. FIG. 1 is an external view showing the basic construction of the intracerebral information measuring device of the present embodiment. FIG. 2 is a schematic sectional view of a subject's head with the intracerebral information measuring device of the present embodiment mounted thereon.

As shown in FIG. 1, the intracerebral information measuring device according to the present embodiment consists of an internally mounted unit 1 and an external measuring unit 10 separated from each other. The internally mounted unit 1 has a sharp-pointed probe section 2 integrated with a roughly disc-shaped head section 3 having a diameter greater than that of the probe section 2. As shown, the internally mounted unit 1 is shaped like a thumbtack (or drawing pin).

As shown in FIG. 2, the internally mounted unit 1A or 1B can be mounted on the subject's head 100 by incising the scalp 101, boring into the skull 102 to create a small hole having a diameter slightly larger than that of the probe section 2A or 213, and inserting the probe section 2A or 213 into the hole until the head section 3A or 3B comes in contact with the skull 102. Subsequently, the incised portion of scalp 101 is sutured to cover the head section 3A or 3B. As a result, the head section 3A or 3B is held between the scalp 101 and the skull 102. The probe section 2A is inserted into the cerebral cortex 103 until its tip directly pierces the cerebrum 104, while the probe section 2B is inserted into a sulcus of the brain 105. The external measuring unit 10A or 10B is typically placed as close to the head section 3A or 3B as possible across the scalp 101. However, in some cases, it can be provided at a more remote location.

FIGS. 3A-3C are schematic sectional views showing three representative forms of the probe section 2.

More specifically, FIG. 3A shows a single-core probe structure in which the probe section 2 consists of an electrode 21 entirely made of a conductive material. The conductive material should preferably be a metal that barely corrodes, such as stainless steel or an alloy containing stainless steel as the chief material. The electrode 21 is intended for the measurement of the cortical field potential over a region near the intracerebral portion where the electrode is placed or over a region near the sulcus of the brain where the electrode is inserted.

FIG. 3B shows a single-core sheath probe structure in which a thin electrode 22 extending to the sharp tip of the probe section 2 is covered with a light guide 23 made of a transparent synthetic resin, quartz glass or similar material. The electrode 22 is exposed only at the tip thereof. This is to measure the local potential at a deep region of the brain where it is inserted or the sulcus of the brain where it is inserted. The light guide 23 is a sort of optical fiber for guiding light (near infrared) introduced from the head section 3 to irradiate the inside of the brain or sulcus of the brain with the light, for receiving the light reflected by, scattered by or transmitted through an inner region of the brain or sulcus of the brain, and for sending the received light to the head section 3. The circumferential surface of the light guide 23 is exposed, so that a portion of light passing through the light guide 23 and hitting its inner circumferential surface at an angle smaller than the total reflection angle penetrates through that surface and illuminates the surrounding area.

FIG. 3C shows a coaxial probe structure in which the light guide 23 of the aforementioned single-core sheath probe structure is covered with a cylindrical electrode 24 made of a conductive material. That is to say, the space between the central electrode 22 and the cylindrical outer electrode 24 is filled with the light guide 23. The outer electrode 24 is terminated at a point near the tip of the probe section 2, leaving the light guide 23 exposed in a sharp-pointed form. Therefore, the light guided from the head section 3 through the light guide 23 exits from the tip portion of the probe section 2. Similar to the electrode 21 shown in FIG. 3A, the outer electrode 24 can be used to measure the cortical field potential over a region near the intracerebral portion where the electrode is stuck or over a region near the sulcus of the brain where the electrode is inserted. Simultaneously, the electrode 22 can be used to measure the local potential at a deep region of the brain where the electrode is stuck or the sulcus of the brain where the electrode is inserted.

In any of the three forms of FIGS. 3A-3C, the probe section 2 may be either a needle-like rigid part or a flexible part that can be moderately bent. As a rough guide, the outer diameter of the probe 2 may be within a range from 100 to 500 micrometers. The length of the probe section 2 can be appropriately determined according to the type of the subject, the depth of the region to be measured, and other factors.

A specific form of the internally mounted unit 1 is hereinafter described. FIG. 4 is a schematic sectional view of an internally mounted unit 1a using the single-core sheath structure shown in FIG. 3B. This unit has no active electrical circuit inside the head section 3. In that sense, the present construction is herein referred to as a passive type.

The head section 3 includes a hollow casing 31 made of a metal (or other conductive materials). This casing 31 is electrically connected to the electrode 22. A substantially conical micro-optic lens 32 (which corresponds to the optical aperture in the present invention) is provided in the casing 31. The pointed end of the micro-optic lens 32 is optically connected to the light guide 23 of the probe section 2, while the spherical portion on the bottom side of the lens 32 is exposed to the outside of the casing 31. As shown in FIG. 4, when the internally mounted unit 1 is provided between the scalp 101 and the skull 102, the spherical portion of the micro-optic lens 32 is in contact with (or close to) the inner surface of the scalp 101.

In this internally mounted unit 1a, the electrode 22 of the probe section 2 inserted in the brain or into the sulcus of the brain senses, for example, the action potential of a nervous tissue in the deep region of the brain or sulcus of the brain and generates an electrical oscillation, which is amplified due to the radiation by the casing 31 and radiated in the form of faint electromagnetic waves. These waves pass through the scalp, to be received by the external measuring unit 10 (which is not shown) located outside the scalp, where the electric signal is reproduced. In the present case, since the electromagnetic waves radiated from the casing 31 are considerably weak, the external measuring unit 10 should be placed as close to the casing 31 as possible across the scalp 101.

As shown in FIG. 4, when near-infrared light is cast from the external measuring unit 10 onto the scalp 101, the light passes through the scalp 101, becomes condensed by the micro-optic lens 32 located underneath, and is sent into the light guide 23. Through this light guide 23, the near-infrared light is delivered into the brain or sulcus of the brain. When the reflected light, scattered light or transmitted light generated inside the brain or sulcus of the brain in response to an emission of the near-infrared light from the probe section 2 of one internally mounted unit 1a enters the light guide 23 of the probe section 2 of another internally mounted unit 1a, the light is guided through the light guide 23 to the micro-optic lens 32, to be emitted through the scalp 101 to the outside. The external measuring unit 10 receives this light and analyzes its intensity change in real time. Thus, an optical topography measurement can be performed.

Figure 5:
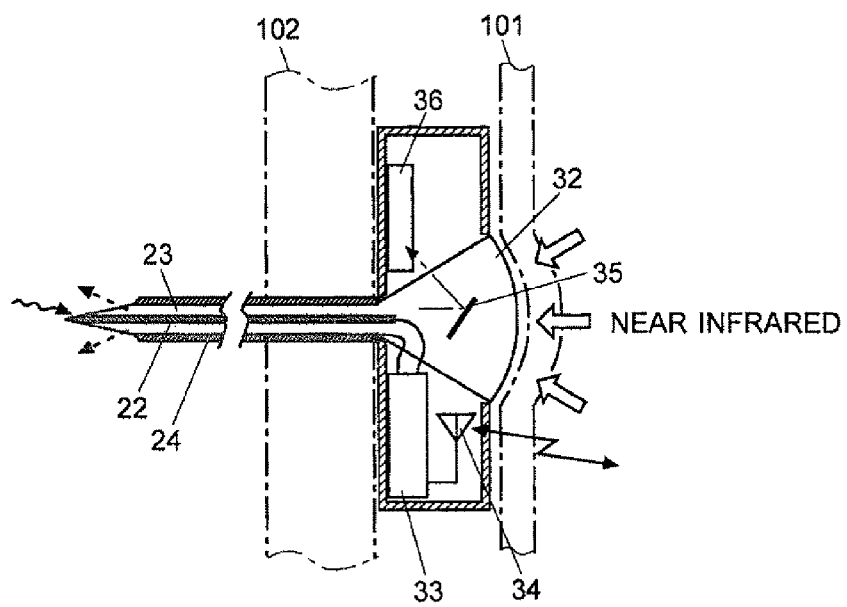
FIG. 5 is a schematic sectional view of one form (active type) of the internally mounted unit using a coaxial probe structure.

FIG. 5 is a schematic sectional view of an internally mounted unit 1b having another construction which uses the coaxial probe structure shown in FIG. 3C. This unit has an active electrical circuit inside the head section 3. In that sense, the present construction is herein referred to as an active type in comparison with the aforementioned passive type.

In the internally mounted unit 1b, the head section 3 contains an electrical circuit unit 33, an antenna 34, and a photo-sensor 36. A mirror 35 for reflecting light coming from the probe section 2 back through the light guide 23 to introduce the light into the photo-sensor 36 is embedded in the micro-optic lens 32. The electrodes 22, 24 and the photo-sensor 36 are electrically connected to the electrical circuit unit 33.

Figure 6:
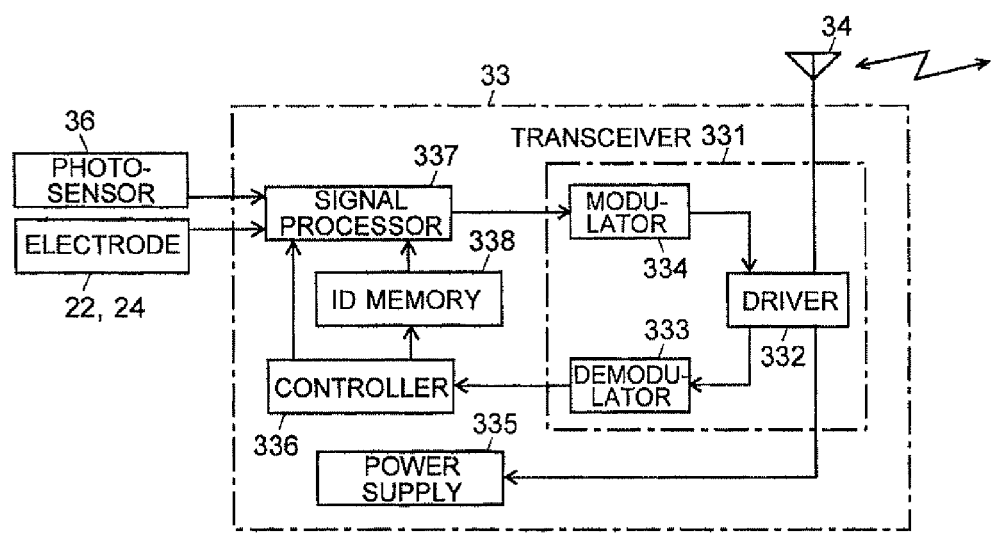
FIG. 6 is a schematic block diagram showing the construction of a built-in electrical circuit unit of the head section.
Figure 7:
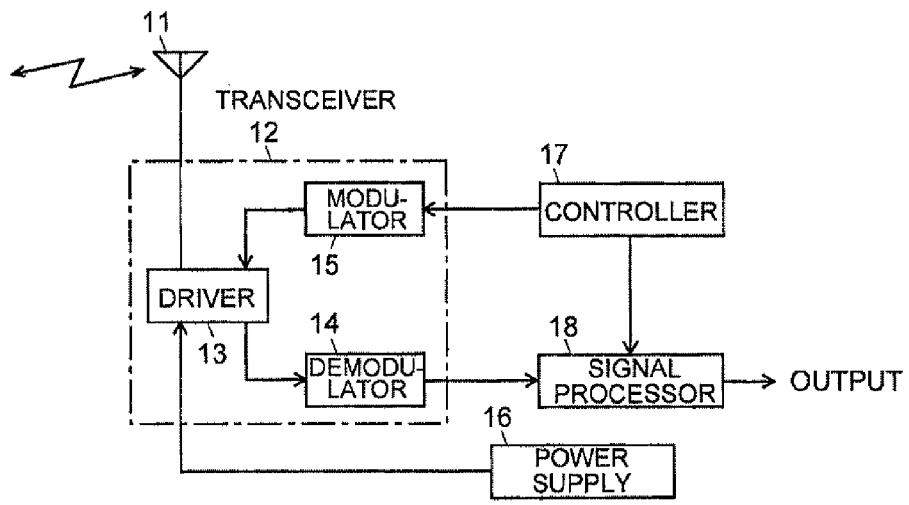
FIG. 7 is a schematic block diagram of an external measuring unit.

FIG. 6 is a schematic block diagram showing the construction of the electrical circuit unit 33. FIG. 7 is a schematic block diagram showing the construction of an external measuring unit 10 to be used for the present internally mounted unit 1b.

The electrical circuit unit 33 has a transceiver 331, a power supplier 335, a controller 336, a signal processor 337 and an ID memory 338. The transceiver 331 includes an antenna driver 332, a modulator 334 and a demodulator 333. Each internally mounted unit 1 is given a unique identification information (ID), which is stored beforehand in the ID memory 338. On the other hand, the external measuring unit 10 has a transceiver 12, a power supplier 16, controller 17 and a signal processor 18. The transceiver 12 includes an antenna driver 13, a modulator 15 and a demodulator 14.

In the external measuring unit 10, the power supplier 16 drives the antenna 11 via the antenna driver 14 so as to radiate electromagnetic waves of a predetermined frequency from the antenna 11. The power supplier 335 of the electric circuit unit 33 receives the electromagnetic waves via the antenna 34 and generates electric power, which is supplied to the other components of the electrical circuit unit 33. This means that the electrical circuit unit 33 has no battery or similar internal power source; it generates a required amount of power from the electromagnetic waves externally supplied via the antenna 34. This circuit is basically the same as the one used in a so-called passive IC tag. It is naturally possible to provide the electrical circuit unit 33 with a built-in battery. However, this is disadvantageous for creating lightweight, long-life devices.

In the external measuring unit 10, a control signal produced by the controller 17 is modulated by the modulator 15 into a predetermined form (e.g. into a signal within a frequency band suitable for radio transmission through the antennae 11 and 34) and transmitted from the antenna 11 via the antenna driver 13. The electrical circuit unit 33 receives this signal through the antenna 34 and demodulates it with the demodulator 333 to extract the original control signal. Based on this control signal, the controller 336 controls the operation of the signal processor 337, ID memory 338 and other components. This operation basically includes reading the ID from the ID memory 338, modulating the ID to a predetermined form by the modulator 334, and transmitting the obtained signal from the antenna 34 via the antenna driver 332. Furthermore, an electric signal collected through the electrodes 22 and 24 or generated by photo-electric conversion in the photo-sensor 36 is amplified by the signal amplifier 337. Additionally, this signal may be multiplexed (e.g. by frequency multiplexing or time-division multiplexing) as needed. The obtained signal is modulated into a predetermined form by the modulator 334 and transmitted from the antenna 34 via the antenna driver 332.

In the external measuring unit 10, the aforementioned radio waves transmitted from the internally mounted unit 1 are received through the antenna 11 and demodulated by the demodulator 14 into the original signal. Then, this signal is processed by the signal processor 18 to separately extract the ID and the electric signals obtained with the electrodes 22, 24 and the photo-sensor 36.

Figure 8:
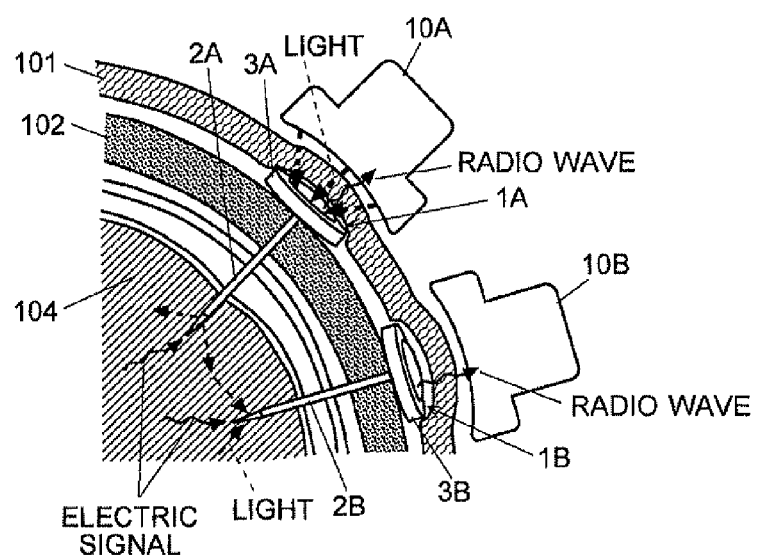
FIG. 8 is a schematic diagram showing one example of the measurement using the internally mounted unit and the external measuring unit shown in FIGS. 5-7.

FIG. 8 is a schematic diagram showing one example of the measurement using the internally mounted unit and the external measuring unit shown in FIGS. 5-7. Though FIG. 8 shows only two internally mounted units 1A and 1B and two external measuring units 10A and 10B, any number of internally mounted units and external measuring units can be simultaneously used. The external measuring unit 10A emits near-infrared light, which passes through the scalp 101 and enters the head section 3A of the internally mounted unit 1A, to be delivered through the light guide in the probe section 2A into the brain. The delivered near-infrared light emits from the tip of the probe section 2A into an inner region of the brain, being reflected or scattered while passing through the brain. A portion of this light reaches the tip of the probe section 2B of the other internally mounted unit 1B and enters the light guide, to be sent to the head section 3B and converted into an electric signal by the photo-sensor 36. This electric signal contains various kinds of information, such as the information relating to the blood flow in the brain.

On the other hand, the internally mounted units 1A and 1B capture electric signals inside the brain with the electrodes 22 and 24 of the probe sections 2A and 2B. The electric signal captured with the electrodes 22 and 24 of the probe section 2A of the internally mounted unit 1A is radio-transmitted to the outside by the electrical circuit unit 33 and the antenna 34 contained in the head section 3A, and received by the external measuring unit 10A. The electric signal detected with the electrodes 22 and 24 of the probe section 2B of the internally mounted unit 1B, and the electric signal produced by photo-electric conversion in the photo-sensor 36, are radio-transmitted to the outside by the electrical circuit unit 33 and the antenna 34 contained in the head section 3B, and received by the external measuring unit 10B. In this manner, both electrical information relating to the brainwaves or other signals and optical information such as optical topography are concurrently collected.

Particularly, the use of the internally mounted unit having the coaxial probe structure shown in FIG. 3C allows the near-infrared light cast onto the scalp 101 to be delivered to a deep region in the brain or sulcus of the brain. In the case of the conventional noninvasive optical tomography, only the surface region of the brain can be covered by the measurement. By contrast, with the present technique, a high-resolution optical topography measurement of a deep region of the brain can be achieved.

In the case of the active-type internally mounted unit 1B shown in FIG. 5, the electric signals or other signals can be amplified in the electrical circuit 33, and any noise mixed in the signals during the transmission can be removed by processing the signals in the external measuring unit. Therefore, compared to the passive type, the active type can produce signals with higher quality and hence is advantageous for improving the sensitivity and resolution of the measurement. Furthermore, this type does not always require the external measuring unit 10 to be extremely close to the internally mounted unit 1, as shown in FIG. 8, since both electric power and electric signals can be transferred over a certain distance.

Furthermore, the present construction allows the signals obtained through the electrodes 22, 24 or other components to be digitized in the electrical circuit unit 33 and transmitted in the form of digital data. Even when many internally mounted units are mounted in the subject's head, each internally mounted unit can be identified by its ID. Therefore, it is possible to provide only one external measuring unit to control all the internally mounted units and process all the signals.

In the case of using a plurality of external measuring units, a means for enabling mutual communication among the external measuring units may be provided to perform a coordinated measurement using the external measuring units. For example, in addition to a simultaneous measurement using all the internally mounted units, it is possible to perform a measurement in which a large number of internally mounted units arranged over the entire surface of the brain are individually controlled so that their operation times are staggered according to a predetermined schedule. Such a network of the internally mounted units makes it possible to perform a complex, sophisticated measurement that cannot be achieved by conventional devices.

In the previous embodiment, the internally mounted unit has only one light guide in its probe section. It is also possible to provide two light guides parallel to each other so as to separate the entrance and exit optical paths (in such a manner that no interference of light occurs between the two light guides). According to this design, a measurement corresponding to the optical topography measurement can be performed with a single internally mounted unit on the subject.

It should be noted that the previous embodiment is a mere example. Any change or modification appropriately made within the spirit of the present invention will evidently fall within the scope of claims of the present application.

EXPLANATION OF NUMERALS 1, 1A, 1B, 1a, 1b . . . Internally Mounted Unit
2, 2A, 2B . . . Probe Section
3, 3A, 3B . . . Head Section
10, 10A, 10B . . . External Measuring Section
11, 34 . . . Antenna
12 . . . Transceiver 13 ... Antenna Driver
14 ... Demodulator
15 ... Modulator
16 ... Power Supplier
17 ... Controller
18 ... Signal Processor
21, 22, 24 ... Electrode
23 ... Light Guide
31 ... Casing
32 ... Micro-Optic Lens
33 ... Electrical Circuit Unit
35 ... Mirror
36 ... Photo-Sensor
331 ... Transceiver
332 ... Antenna Driver
333 ... Demodulator
334 ... Modulator
335 ... Power Supplier
336 ... Controller
337 ... Signal Processor
338 ... ID Memory
100 ... Head
101 ... Scalp
102 ... Skull
103 ... Cerebral Cortex
104 ... Cerebrum
105 ... Sulcus of the brain

The invention claimed is:

1. An intracerebral information measuring device for collecting information relating to an inside of a brain of a subject, comprising:
    a) an internally mounted unit including: a probe section being designed to be inserted in the brain or into a sulcus of the brain through a hole bored in a skull of the subject, the probe section having an electrode for capturing at least an electric signal in a surrounding area; and a head section integrated with one end of the probe section, the head section being designed to be held between the skull and the scalp of the subject and having a signal transmitter for wirelessly sending at least an electric signal captured with the electrode to an outside of the scalp; and
    b) an external measuring unit to be placed outside the scalp of the subject, for receiving the signal sent from the signal transmitter of the head section through the scalp,
    wherein the signal transmitter consists of a hollow casing made of a conductive material and electrically connected to the electrode, and the hollow casing radiates an electric oscillation obtained with the electrode in a form of electromagnetic waves.

2. The intracerebral information measuring device according to claim 1, wherein the head section has an optical aperture, and the probe section has a waveguide optically coupled to the optical aperture.

3. The intracerebral information measuring device according to claim 2, wherein the external measuring unit includes an irradiator for casting near-infrared light for an optical topography measurement through the scalp of the subject onto the head section of the internally mounted unit.

4. The intracerebral information measuring device according to claim 1, wherein the head section has an optical aperture, the electrode is a long and narrow electrode having a circumferential surface, and the probe section includes a waveguide optically coupled to the optical aperture and covering the circumferential surface of the electrode except a tip portion of the electrode.

5. The intracerebral information measuring device according to claim 1, wherein the head section has an optical aperture, the electrode is a long and narrow electrode having a circumferential surface, and the probe section includes: a waveguide optically coupled to the optical aperture and covering the circumferential surface of the electrode except a tip portion of the electrode; and another cylindrical electrode surrounding a circumferential surface of the waveguide.

* * * * *